United States Patent [19]

Spangler et al.

[11] 4,445,038

[45] Apr. 24, 1984

[54] APPARATUS FOR SIMULTANEOUS DETECTION OF POSITIVE AND NEGATIVE IONS IN ION MOBILITY SPECTROMETRY

[75] Inventors: Glenn E. Spangler, Lutherville; John F. Wroten, Jr., Towson, both of Md.

[73] Assignee: The Bendix Corporation, Southfield, Mich.

[21] Appl. No.: 265,745

[22] Filed: May 21, 1981

Related U.S. Application Data

[63] Continuation of Ser. No. 80,888, Oct. 1, 1979.

[51] Int. Cl.³ .............................................. G01N 27/66
[52] U.S. Cl. ..................................... 250/382; 250/287; 250/381; 250/385
[58] Field of Search ............... 250/282, 283, 285, 286, 250/287, 381, 382, 384, 385

[56] References Cited

U.S. PATENT DOCUMENTS

| 2,999,157 | 9/1961 | Rosenstock | 250/287 |
| 3,307,033 | 2/1967 | Vestal | 250/287 |
| 3,626,180 | 12/1971 | Caroll et al. | |
| 3,626,181 | 12/1971 | Wernlund | 250/287 |
| 4,136,280 | 1/1979 | Hunt et al. | 250/282 |
| 4,266,127 | 5/1981 | Chang | 250/288 |

OTHER PUBLICATIONS

Guthrie, ed., "Vacuum Equipment and Techniques", McGraw-Hill, N.Y., 1949, pp. 4–7.

Primary Examiner—Alfred E. Smith
Assistant Examiner—Carolyn E. Fields
Attorney, Agent, or Firm—W. G. Christoforo; Bruce L. Lamb

[57] ABSTRACT

An ion mobility detector has dual drift regions respectively on either side of a centrally located reaction region and respectively separated therefrom by dual shutter grids. Each drift region terminates in a Faraday cup. An ion accelerating electrical field gradient is provided between the Faraday cups so that negative ions are drawn into one drift region and positively charged ions are drawn into the other drift region.

2 Claims, 1 Drawing Figure

APPARATUS FOR SIMULTANEOUS DETECTION OF POSITIVE AND NEGATIVE IONS IN ION MOBILITY SPECTROMETRY

This application is a continuation of application Ser. No. 80,888 filed Oct. 1, 1979.

FIELD OF THE INVENTION

This invention relates to ion mobility detectors and more particularly to such instruments which can simultaneously detect both positive and negative product ions formed from a common sample.

BACKGROUND OF THE INVENTION

Plasma chromatographs are electrical devices such as ion mobility spectrometers or detectors capable of detecting trace levels of vapor or gas in gaseous mixtures. The configuration of such a detector includes a cell consisting of ionization, reaction, and drift regions along with a shutter grid and a Faraday ion collector or cup and associated processing electronics. The trace vapors or gases are ionized in the reaction region to produce product ions which are sorted according to mobility in the drift region. The mobility of a given ion is inversely proportional to the time it takes to traverse the drift region under the influence of an electrostatic field. Present ion mobility detectors are capable of detecting either positive or negative ions but not both at the same time. Generally, the operation of an ion mobility detector is similar to the operation of a time of flight mass spectrometer, the obvious difference being that a time of flight mass spectrometer operates under vacuum conditions where the mean free path of the contained gases is many times the dimensions of the gas container, while the ion mobility detector operates generally at atmospheric pressure where the mean free path of the contained gases is a small fraction of the dimensions of the container. More particularly, a carrier gas, normally purified atmospheric air, is introduced into the ion mobility detector with a gaseous sample of a material whose identify is to be characterized by the ion mobility detector. This gaseous mixture is introduced into the aformentioned reaction region so that it flows past and is exposed to an ionization source. As a result, portions of both the carrier gas and the sample are directly ionized by the ionization source. However, as known to those practicing in this art, the characteristics of the carrier gas and the sample are usually such that the molecules of the carrier gas are more easily directly ionized by the ionization source than are molecules of the sample. Initially the ions are contained within the reaction region because the shutter grid is electrically charged to repel the ions. Since the mean free path of the gas molecules within the reaction region is many times smaller than the dimensions of the region there are multiple collisions between the molecules of the carrier and sample gases. As also known to those skilled in the art, the tendency of these collisions is to transfer the ion charge from the carrier molecules to the sample molecules, thereby ionizing the sample gas mainly by this secondary ionization process.

The charged particles or ions, now mainly derivatives of the sample, are accelerated to a terminal velocity under the influence of a field potential gradient within the reaction region towards an ion injection grid shutter which separates the reaction region from the drift region. As previously mentioned, the shutter grid is normally electrically charged to repel ions and thus prevent the transfer of ions from the reaction region to the drift region. Periodically, the shutter grid is energized for a short time period to permit a pulse of ions to pass therethrough into the drift region. Here, the ions, under the influence of an electrostatic drift field, are accelerated to an electrometer detector which terminates the drift region. The time of arrival of each ion at the electrometer detector, relative to the time the shutter grid was opened, is determined by the ion's mobility through the nonionized gas occupying the drift region. The heavier ions move more slowly through the drift region and arrive at the electrometer detector after longer drift times than lighter ions. It is thus possible to characterize the ions and hence the sample by observing the time between the opening of the shutter grid and the arrival of ions at the electrometer detector.

The ion mobility detector is normally in the form of a hollow cylindrical structure which defines the various regions. The electrical field gradient within the regions is such as to cause either positive or negative ions to drift towards the electrometer detector. For example, if negative ions are to be detected then a field gradient of a first polarity is used. If positive ions are to be detected then a field gradient of opposite polarity is used.

Problems associated with using ion mobility detectors for environmental sampling are sensitivity and specificity to the sample compound of interest. In particular, more than one compound is often of interest during the detection process. Many times, certain of these compounds are more sensitive to the positive ion spectrum, others are more sensitive in the negative ion spectrum, and still others have characteristic signatures in both spectra. Under these conditions it is desirable that both positive and negative ions be detected from a common sample.

SUMMARY OF THE INVENTION

The present invention is a new and improved ion mobility detector which permits both positive and negative ions from a common sample to be detected. This new ion mobility detector comprises two separate and distinct drift regions which are fed ions from a single reaction region which is located between the two drift regions. Two shutter grids respectively divide the reaction region from the drift regions. Opposite each shutter grid so as to terminate its associated drift regions are two Faraday cups attached to electrometer detectors. The form of the ion mobility detector is generally cylindrical with the various regions arranged serially along the longitudinal axis of the cylinder. An electrical field gradient is applied along the cylinder axis.

The sample, which is to be characterized by the ion mobility detector, and the carrier gas, usually purified or atmospheric air, are flowed through the reaction region where the sample is ionized as in the prior ion mobility detector art. Under the influence of the applied electrical field gradient the negative ions are accelerated in a first direction towards a first shutter grid while the positive ions are accelerated in a second opposite direction towards a second shutter grid. When the shutter grids are opened to pass ions into their respective drift regions, either simultaneously or in sequence, negative ions enter one drift region while positive ions enter the other drift region and drift under the influence of the applied field gradient towards the respective Faraday cups.

It is an object of this invention to provide an ion mobility detector which responds to both positively and negatively charged ions produced from a common source.

BRIEF DESCRIPTION OF THE DRAWING

The drawing is a diagramatic longitudinal sectional view which illustrates an ion mobility detector employing the means of the present invention.

DESCRIPTION OF THE PREFERRED EMBODIMENT

Figure 1:
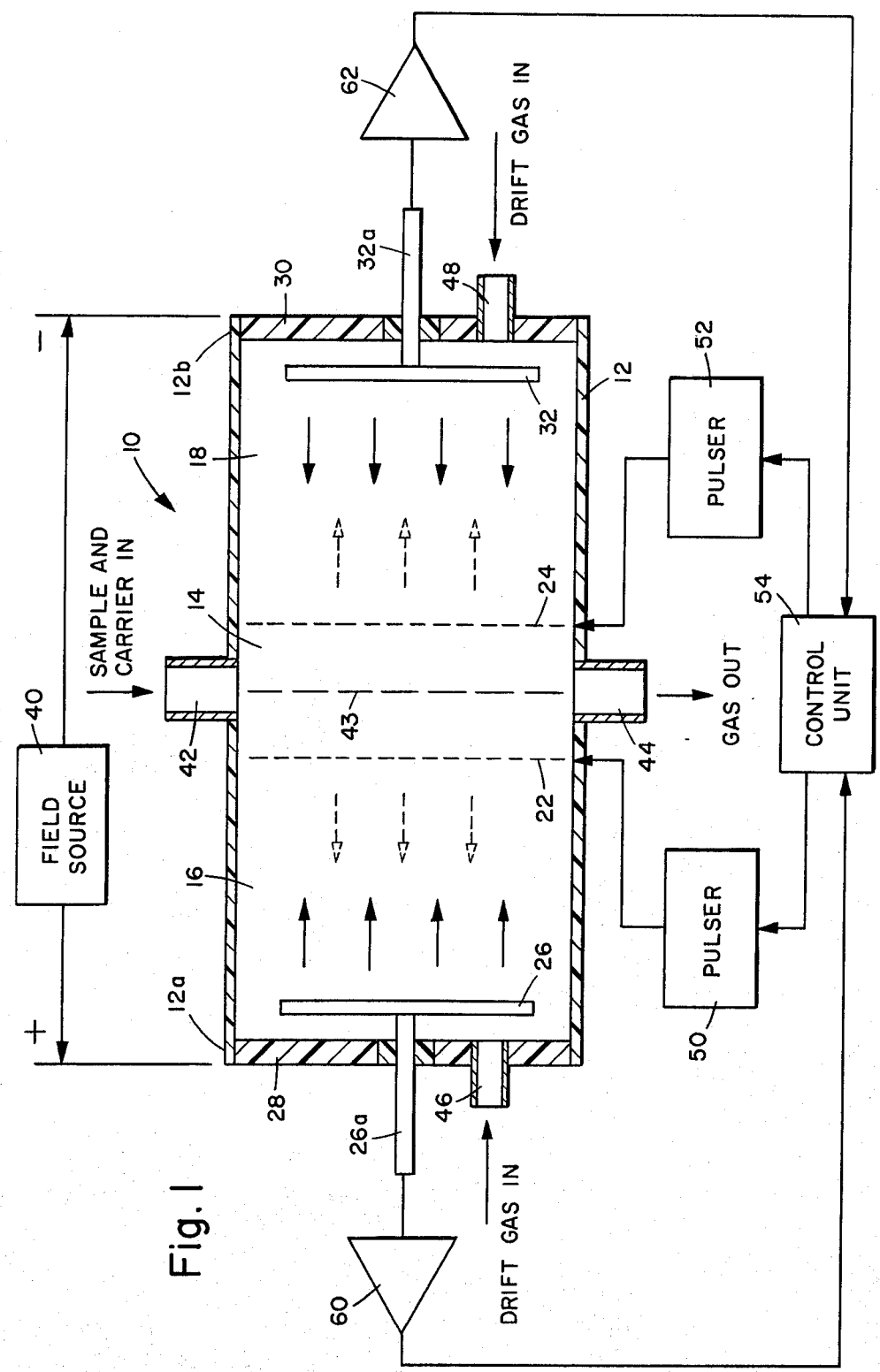

Referring to the figure, an ion mobility detector according to the present invention is seen at 10 to be comprised of a cylindrical structure 12 with end walls 28 and 30 and divided in its interior portion into a centrally located ion generation and reaction region 14 which is bounded by structure 12 and shutter grids 22 and 24 of the type known in the art, which also separate reaction region 14 respectively from drift regions 16 and 18 located on either side thereof. Drift region 16 is bounded circumferentially by cylindrical structure 12, at one end by shutter grid 22 and at the other end by Faraday cup 26. Drift region 18 is bounded circumferentially by cylindrical structure 12, at one end by shutter grid 24 and at the other end by Faraday cup 32.

An electrical field gradient is impressed along the longitudinal axis of ion mobility detector 10 from Faraday cup 26 to Faraday cup 32 by a source 40. The means for generating the electrical field gradient can comprise one of the various means known in the art. For example, the cylindrical structures of ion mobility detectors are normally built up of a plurality of electrically conductive guard rings interleaved with insulating rings. Descending voltages are applied to successive guard rings from end 12a to end 12b to thereby generate the appropriate electrical field gradient in the ion mobility detector. A recent development in the plasma chromatography arts has seen the appearance of a one piece ion accelerator wherein structure 12 is made up of one or more ceramic tubes whose interior surface comprises a continuous thick film resistor which in the present embodiment extends from end 12a to end 12b. The terminals of a voltage source are connected respectively to annular electrical terminals which terminate the thick film resistor at ends 12a and 12b so that there is a continuous voltage gradient along the interior surface of structure 12 to thereby generate the appropriate electrical field gradient. In any event the means for generating the electrical field gradient does not comprise the substance of this invention.

A carrier gas with a sample which is to be characterized by the ion mobility detector is admitted into reaction region 14 through a tube 42. The sample carrier gas flows past an ionizer 43 to ionize thereby principally the carrier gas as explained earlier. Various of the ionizers known in the art are suitable for use in this invention. For example, a radioactive source such as $^{63}$Ni or a corona discharge can be used as ionizer 43. As also explained earlier, by secondary collisions between the molecules of the sample and the ionized molecules of the carrier the sample is ionized within reaction region 14 with the positive ions drifting to the right as seen in the figure and the negative ions drifting to the left as seen in the figure, under the influence of the electrical field gradient. Initially shutter grids 22 and 24 are biased by pulsers 50 and 52 respectively so that ions are contained within the reaction region 14. At times determined by control unit 54 the pulsers 50 and 52 either simultaneously or in sequence energize their associated shutter grids to pass pulses of ions therethrough into associated drift region 16 and 18 under the influence of the electrical field gradient. The ions flow in the direction of the dashed arrows, the negative charged ions to the left through drift region 16 to Faraday cup 26 and the positively charged ions to the right through drift region 18 to Faraday cup 32. The ions collide with the Faraday cups and upon colliding therewith are deionized to cause an electrical current to flow in the circuit comprised of Faraday cup 26 and stem 26a or Faraday cup 32 and stem 32a as appropriate. The currents are amplified by amplifiers 60 and 62 respectively with the output signals therefrom being applied to control unit 54.

Control unit 54 having noted the time at which the shutter grid was pulsed to pass ions now notes the arrival time of the ions at the appropriate Faraday cup and, according to normal ion mobility detector technique, characterizes the ions by the elapsed or drift time thereof.

A drift gas which can be purified or atmospheric air is admitted respectively into drift regions 16 and 18 through end walls 28 and 30 and more particularly through ports 46 and 48. The drift gas moves in the direction of the solid arrows towards the reaction region to sweep the non-ionized molecules out of the ion mobility detector and through outlet port 44 which is located to provide egress from the reaction region 14. In addition nonionized molecules of the sample and the carrier gas admitted through port 42 also exit though port 44.

The means for injecting the various gasses into the ion mobility detector can optionally be provided by a vacuum pump operating at port 44 or by pressurizing ports 42, 46 and 48 or any suitable combination thereof as known to those skilled in the art.

Having described this embodiment of our invention various modifications and alterations thereof will now be obvious to one skilled in the art. Accordingly, we claim as our invention that property encompassed by the true spirit and scope of the appended claims.

The invention claimed is:

1. In means for characterizing the mobility of ions by measuring the drift time of ions urged by a field gradient through a drift region containing non-ionized gas whose molecules have a mean free path many times smaller than said drift region, an improvement for characterizing the mobility of both negative and positive ions from a common sample mixed with a carrier gas comprising:
    a first drift region;
    a second drift region;
    a reaction region centrally located between said first and second drift regions;
    a first shutter grid separating said reaction region from said first drift region and normally biased to prevent positive ions from passing therethrough;
    a second shutter grid separating said reaction region from said second drift region and normally biased to prevent negative ions from passing therethrough;
    entrance means for allowing molecules of said sample and carrier to enter said reaction region;
    means primarily ionizing the molecules of said carrier in said reaction region, the molecules of said sample being secondarily ionized within said reaction region by collisions with the ionized carrier molecules whereby said ionized carrier molecules are deionized;

first ion detector means in said first drift region opposite said first shutter grid for deionizing positive ions arriving thereat and providing an output signal indicative of said deionized positive ions;

second ion detector means in said second drift region opposite said second shutter grid for deionizing negative ions arriving thereat and providing an output signal indicative of said deionized negative ions;

means for impressing a field gradient from said first means to said second means whereby positive ions are urged toward said first means and negative ions toward said second means;

means for momentarily biasing said first shutter grid to allow positive ions to pass therethrough from said reaction region into said first drift region and for momentarily biasing said second shutter grid to allow negative ions to pass therethrough from said reaction region into said second drift region whereby positive ions are urged by said field gradient through said first drift region to said first ion detector means where they are detected and whereby negative ions are urged by said field gradient through said second drift region to said second ion detector means where they are detected; and means noting the elapsed time between the biasing of said first shutter grid and the detection of positive ions at said first means for characterizing the mobility of said positive ions and for noting the elapsed time between the biasing of said second shutter grid and the detection of negative ions at said second means for characterizing the mobility of said negative ions.

2. The improvement of claim 1 wherein said means for characterizing comprises a structure encompassing an approximately cylindrical enclosed volume divided into said first and second drift regions with said reaction region located therebetween, said regions being arranged serially along the longitudinal axis of said cylindrical enclosed volume.

* * * * *